United States Patent [19]

Hamilton et al.

[11] Patent Number: 4,740,159

[45] Date of Patent: Apr. 26, 1988

[54] METHOD FOR MAKING A DENTAL IMPRESSION

[75] Inventors: James C. Hamilton, Ann Arbor; Duncan E. Waller; Christina L. Semkow, both of Ypsilanti, all of Mich.

[73] Assignee: Kerr Manufacturing Company, Romulus, Mich.

[21] Appl. No.: 74,877

[22] Filed: Jul. 17, 1987

Related U.S. Application Data

[63] Continuation of Ser. No. 900,110, Aug. 25, 1986, abandoned.

[51] Int. Cl.$^4$ ................................................ A61C 9/00
[52] U.S. Cl. ........................................................ 433/37
[58] Field of Search ........................ 433/199.1, 175, 37, 433/201.1, 215, 168, 214

[56] References Cited

U.S. PATENT DOCUMENTS 4,468,202  8/1984  Cohen ................................. 433/199
4,543,063  9/1985  Cohen ................................. 433/175

Primary Examiner—Robert Peshock
Attorney, Agent, or Firm—Marjama & Pincelli

[57] ABSTRACT

A method of forming a two step dental impression which comprises applying a light curable impression material to a portion of the oral cavity of interest to form an initial impression while exposing said impression material to a source of activating light to set said impression material followed by applying a chemically cured impression material over said light cured impression material and allowed said chemically cured impression material to set and bond with said light curable material and removing the resulting composite impression from said oral cavity.

7 Claims, No Drawings

METHOD FOR MAKING A DENTAL IMPRESSION

This is a continuation of application Ser. No. 900,110 filed Aug. 25, 1986 and now abandoned.

BACKGROUND OF THE INVENTION

The present invention relates to a system and method for forming an intraoral impression of tooth structure and soft tissue.

The invention overcomes two common difficulties associated with light cured impression material of the prior art. The first difficulty is the problem associated with attempting to cure the entire mass of the light cured impression material at one time including the material underneath the gingival margin. A second problem is that associated with the light cured material that is expelled from the tray during the seating of the tray and cannot be exposed to the light source.

As will become apparent from the following disclosure, the present invention overcomes the above problems associated with the prior art in addition to providing a number of unique advantages relating to ease and convenience of handling impression materials and better and more efficient curing.

DESCRIPTION OF INVENTION

A system and method are described for facilitating the forming of an intraoral impression of tooth structure and soft tissue. The mouth is prepared in the same manner as is currently done in the dental art to take an impression. Instead of injecting a conventional chemically activated low visosity impression material, a light activated, low viscosity material is first used. When the parts of the oral cavity that are of interest, such as the prepared teeth, are covered with the light-cured impression material, the material is then set with visible light energy in a suitable range of about 370 to 550 nanometers. A suitable light source comprises the Kerr Command Light TM, sold by Kerr Manufacturing Company. As the light cured material is being set, a chemically cured material is mixed (either a base-catalyst or a base-accelerator system) which is thixotropic. The material is placed in a conventional or custom impression tray such as a Kerr Manufacturing Company Kwik Tray TM or Formatray TM and seated in the mouth covering the set light cured impression material and the surrounding oral tissues. When the chemically cured impression material is set, the tray containing the light cured impression material along with the chemically cured impression material is removed from the mouth as one unit.

The following suitable light cured impression materials may be used in forming the initial impression:

Adducts of long chain aliphatic polyester polyols with aliphatic diisocyanates, endcapped with hydroxy functional acrylates or methacrylates, and modified by the incorporation of photosensitizing components, plasticizers, fillers pigments, tack reducing additives and stabilizers, as described in assignee's U.S. patent application Ser. No. 890,049 filed in the U.S. Patent Office on July 28, 1986, entitled Visible Light Cured Impression Material incorporated herein by reference.

A specific suitable light cured impression material comprises the following which is disclosed in Example 2 of the above-mentioned patent application.

| | |
|---|---|
| Rucoflex S-1011-55* | 456.0 parts (.456 equiv.) |
| 1,6 Hexanediisocyanate | 63.8 parts (.760 equiv.) |
| 2-Hydroxypropylmethacrylate | 43.8 parts (.304 equiv.) |
| Santicizer 261** | 338.0 parts |
| Dimethylaminobenzaldehyde | 4.6 parts |
| Aerosil R-972*** | 19.0 parts |
| Quso**** | 68.4 parts |
| Dibutyltindilaurate (T-12) | 0.4 parts |
| Irganox 1010***** | 0.2 parts |
| Modaflow****** | 0.9 parts |
| Camphroquinone | 0.6 parts |
| Meteor Cobalt Blue (Harshaw Chemical) | 2.0 parts |

*A polymeric 2, 2'-oxybis [ethanol] hexanedioic acid ester. ($C_6H_{10}O_4C_4H_{10}O_3$)
**(Octyl Benzyl Phthalate available from Monsanto Chemical Company
***A hydrophobic submicron synthetic amorphous precipitated silica available from DeGussa.
****Quso WR 55 from PQ Corporation, a synthetic amorphous precipitated silica.
*****Tetrakis (Methylene (3, 5-Di-Tert-Butyl-4-Hydroxy hydrocinnamate)) Methane
******Ethyl acrylate and 2-ethyl hexyl acrylate copolymer The following chemically cured impression materials may be used in forming the second portion of the composite impression of the present invention:

Two component acrylic functional materials having the following general composition and used in approximate 10:1 base to catalyst ratio.

| | WT. % |
|---|---|
| BASE PASTE | |
| Difunctional urethane methacrylate prepolymer | 30–60 |
| Diluent acrylic functional monomer | 3–15 |
| Acrylic functional tertiary amine | 0.2–5.0 |
| Filler(s) | 20–70 |
| Pigment(s) | 0.1–3.0 |
| EXAMPLE | |
| Polyesterpolyolhexamethylenediisocyanatehydroxypropylmethacrylate adduct | 40.0 |
| Polypropyleneglycoldimethacrylate | 8.5 |
| Dimethylaminoethylmethacrylate | 1.0 |
| Micronized silica filler | 50.0 |
| FD & C Blue #2 Lake pigment | 0.5 |
| | 100.0 |
| CATALYST PASTE | |
| Acrylic functional crosslinking monomer | 30–60 |
| Acyl peroxide | 0.5–10.0 |
| Filler(s) | 20–70 |
| Inhibitor/stabilizer | 0.01–0.5 |
| EXAMPLE | |
| Ethoxylated Bisphenol A Dimethacrylate | 50.0 |
| Benzoyl Peroxide | 4.9 |
| Micronized silica filler | 45.0 |
| Inhibitor(s) (4-Methoxyphenol/Irganox 1010 blend) | 0.1 |
| | 100.0 |

The two component chemically cured material is intended to bond to a single component visible light activated acrylic functional impression material in a two step technique, wherein a light bodied visible light activated impression material is first injected around the dentition and cured, after which a mix of the two component impression material is placed in a tray over the cured light bodied material and allowed to polymerize and bond to it, to provide dimensional stability. The attachment between the light cured impression material and chemically cured impression material is essentially by chemical bonding between the two.

This two component acrylic functional impression material is cured by free radical polymerization, the free radicals being generated by the interaction of a soluble acyl peroxide in one component with a soluble tertiary amine in the other component by the classic Swenck redox mechanism.

Since the single component light activated impression material cures with a slightly air-inhibited surface, the two component material placed over it acts as an air excluder and enables a strong interfacial bond to develop by copolymerization as the two component material polymerizes.

Compositionally, the base paste, which contains the tertiary amine also contains a difunctional aliphatic long-chain urethane methacrylate prepolymer, a diluent monomer, filler(s) and pigment.

The catalyst, which contains the acyl peroxide, contains an acrylic functional crosslinking monomer plus inhibitor(s) to control the rate of reaction and suppress autopolymerization tendencies of this paste during shelf life.

The following example specifically illustrates one embodiment of the present invention.

EXAMPLE

The gingiva around the tooth being impressed is retracted using a gingival retraction cord. After sufficient time has elapsed for the gingiva to retract, the cord is removed and the light-cured impression material described above, pre-packaged in a light-proof syringe is injected into the sulcus around the tooth. This material is then cured with visible light from a Kerr Command curing unit using a standard 5 mm light guide. While the light-cured material is being injected around the tooth, the base and catalyst of the chemically-activated impression material described in the above examples are mixed together and loaded into a Kerr Kwik-Tray TM. After the light-cured material has set, the mixed chemically-activated material is placed directly over the set light-cured material. When the chemically-activated material has set, the tray is removed from the mouth, taking with it the entrapped chemically-bonded, light-cured impression material.

An impression of the prepared tooth is captured in the light-cured material while adjacent teeth, as well as surrounding tissue, are captured in the chemically-activated material.

This invention overcomes two difficulties associated with light cured impression materials. One is curing all the mass of the light cured impression material at one time including the material underneath the gingival margin. The second one has to do with light curing the material that was expelled from the tray during the seating of the tray. The present invention provides a number of additional advantages: For example, the dentist will not need to mix a low viscosity material, thus the light cured material will be free of voids usually encountered when air is accidentally mixed into the material during the mixing of the base and catalyst portions of an impression material system. This material can be prepackaged in a light proof syringe, with light proof disposable tips. The dentist can therefore inject the material directly into the mouth at the exact location of interest. The dentist can take as much or as little time as necessary to inject the light bodied material and then gain a command set by just exposing that material to the visible light source. Because only a thin layer of material needs to be cured in this situation, light from a regular dental composite restorative curing unit such as a Kerr Command Light can be used to polymerize the impression material. Curing wand tips specially designed can also be used. These would take the form of "U" shaped channel so the light cured impression material would be cured from three sides at the same time. The open portion of the "U" channel would be placed over the tooth covered with light cured impression material. By using a chemically cured product to take an impression over the light cured product, the concern about uncured material that is pushed beyond the edge of the tray and underneath the gingival margin is obviated.

Although particular embodiments of the present invention have been disclosed herein for purposes of explanation, further modifications or variations thereof will be apparent to those skilled in the art to which this invention pertains.

What is claimed is:
1. A method of forming a two step dental impression which comprises:
 (a) applying a light curable impression material to a portion of the oral cavity of interest to form an initial impression while exposing said impression material to a source of activating light to set said impression material;
 (b) applying a chemically cured impression material over said light cured impression material and allowed said chemically cured impression material to set and bond with said light curable material; and
 (c) removing the resulting composite impression from said oral cavity.

2. A method of forming a composite dental impression which comprises:
 (a) applying a light curable impression material to a portion of the oral cavity of interest to form an initial impression while exposing said impression material to a source of activating light to at least partially set said impression material;
 (b) placing a chemically cured impression material in a dental tray and seating said tray over said light cured impression material and allowed said chemically cured impression material to set and bond with said light curable material; and
 (c) removing the resulting two step impression from said oral cavity.

3. A method of forming a two step dental impression which comprises:
 (a) applying a light curable impression material to a portion of the oral cavity of interest to form an initial impression while exposing said impression material to a source of visible light in the range of about 370 to 550 nanometers to at least partially set said impression material;
 (b) applying a chemically cured impression material over said light cured impression material and allowing said chemically cured impression material to set and bond with said light curable material; and
 (c) removing the resulting two step impression from said oral cavity.

4. A method of forming a two step dental impression which comprises:
 (a) applying a light curable impression material to a portion of the oral cavity of interest to form an initial impression while exposing said impression material to a source of visible light to at least partially set said impression material;
 (b) placing a chemically cured impression material in a dental tray and seating said tray over said light cured impression material and allowed said chemically cured impression material to set and bond with said light curable material; and (c) removing the resulting two step impression from said oral cavity.

5. A method of forming a two step dental impression which comprises:
   (a) applying a light curable impression material which is an adduct of a long chain aliphatic polyester polyol with an alyphatic diisocyanate, endcapped with a hydroxy functional acrylate or methacrylate, and modified by the incorporation of photosensitizing components, plasticizers, fillers, pigments, tack reducing additives and stabilizers to a portion of the oral cavity of interest to form an initial impression while exposing said impression material to a source of activating light to at least partially set said impression material;
   (b) applying a chemically cured two component acrylic functional impression material over said light cured impression material and allowed said chemically cured impression material to set and bond with said light curable material; and
   (c) removing the resulting two step impression from said oral cavity.

6. The method of claim 5 in which the two component impression material comprises base and catalyst pastes of the following broad description, mixed in a suitable ratio:

|  | WT. % |
|---|---|
| BASE PASTE | |
| Difunctional urethane methacrylate prepolymer | 30–60 |
| Diluent acrylic functional monomer | 3–15 |
| Acrylic functional tertiary amine | 0.2–5.0 |
| Filler(s) | 20–70 |
| Pigment(s) | 0.1–3.0 |
| CATALYST PASTE | |
| Acrylic functional crosslinking monomer | 30–60 |
| Acyl peroxide | 0.5–10.0 |
| Filler(s) | 20–70 |
| Inhibitor/stabilizer | 0.01–0.5 |

7. The method of claim 1 in which the light curable impression material comprises an adduct of a long chain aliphatic polyester polyol with an aliphatic diisocyanate, endcapped with a hydroxy functional acrylate or methacrylate, and modified by the incorporation of photosensitizing components, plasticizers, fillers, pigments, tack reducing additives and stabilizers and the chemically curable impression material comprises base and catalyst pastes of the following description, mixed in a suitable ratio:

|  | WT. % |
|---|---|
| BASE PASTE | |
| Difunctional urethane methacrylate prepolymer | 30–60 |
| Diluent acrylic functional monomer | 3–15 |
| Acrylic functional tertiary amine | 0.2–5.0 |
| Filler(s) | 20–70 |
| Pigment(s) | 0.1–3.0 |
| CATALYST PASTE | |
| Acrylic functional crosslinking monomer | 30–60 |
| Acyl peroxide | 0.5–10.0 |
| Filler(s) | 20–70 |
| Inhibitor/stabilizer | 0.01–0.5 |

* * * * *